United States Patent
Zhang et al.

(10) Patent No.: US 11,600,389 B2
(45) Date of Patent: Mar. 7, 2023

(54) QUESTION GENERATING METHOD AND APPARATUS, INQUIRING DIAGNOSIS SYSTEM, AND COMPUTER READABLE STORAGE MEDIUM

(71) Applicant: BOE TECHNOLOGY GROUP CO., LTD., Beijing (CN)

(72) Inventors: Zhenzhong Zhang, Beijing (CN); Xue Chen, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 519 days.

(21) Appl. No.: 16/640,267

(22) PCT Filed: Mar. 19, 2019

(86) PCT No.: PCT/CN2019/078734
§ 371 (c)(1),
(2) Date: Feb. 19, 2020

(87) PCT Pub. No.: WO2020/186458
PCT Pub. Date: Sep. 24, 2020

(65) Prior Publication Data
US 2021/0034305 A1   Feb. 4, 2021

(51) Int. Cl.
*G16H 50/20* (2018.01)
*G06N 7/00* (2006.01)
(Continued)

(52) U.S. Cl.
CPC ............ *G16H 50/20* (2018.01); *G06F 40/35* (2020.01); *G06N 3/0454* (2013.01); *G06N 7/005* (2013.01)

(58) Field of Classification Search
CPC ... G06F 1/00–2221/2153; G16H 10/00–80/00; G09B 1/00–29/14
See application file for complete search history.

(56) References Cited

U.S. PATENT DOCUMENTS 10,387,575 B1 *   8/2019   Shen ................ G06F 40/35
10,713,289 B1 *   7/2020   Mishra ............. G06F 40/30
(Continued)

FOREIGN PATENT DOCUMENTS

CN   101286161 A   10/2008
CN   105893523 A   8/2016
(Continued)

OTHER PUBLICATIONS

Prasad et al., "A Personalized Medical Assistant Chatbot: MediBot," IJSTE—International Journal of Science Technology & Engineering | vol. 5 | Issue 7 | Jan. 2019; ISSN (online): 2349-784X. (Year: 2019).*

(Continued)

*Primary Examiner* — Jonathon A. Szumny
(74) *Attorney, Agent, or Firm* — The Webb Law Firm

(57) ABSTRACT

The present disclosure relates to a question generating method and apparatus, an inquiring diagnosis system, and a computer readable storage medium. The question generating apparatus includes at least one processor, the at least one processor being configured to: acquire a candidate question set Q; calculate an information value of each candidate question in the candidate question set Q; and generate at least one question according to the information value of each candidate question.

18 Claims, 2 Drawing Sheets

(51) Int. Cl.
*G06N 3/04* (2006.01)
*G06F 40/35* (2020.01)

(56) References Cited

U.S. PATENT DOCUMENTS

| | | | |
|---|---|---|---|
| 2005/0197988 A1* | 9/2005 | Bublitz | G06Q 30/0201 |
| | | | 706/46 |
| 2007/0207449 A1* | 9/2007 | Feierstein | G09B 7/02 |
| | | | 434/323 |
| 2014/0052722 A1* | 2/2014 | Bertsimas | G16H 10/20 |
| | | | 707/733 |
| 2014/0057241 A1* | 2/2014 | Rapp | G09B 7/02 |
| | | | 434/353 |
| 2015/0324492 A1 | 11/2015 | Iorio et al. | |
| 2015/0332021 A1* | 11/2015 | Godla | G16H 10/60 |
| | | | 705/3 |
| 2016/0371663 A1* | 12/2016 | Knuteson | G06Q 20/102 |
| 2017/0116870 A1* | 4/2017 | Brem | G09B 5/04 |
| 2017/0364804 A1 | 12/2017 | Beller et al. | |
| 2018/0137854 A1* | 5/2018 | Perez | G06F 40/35 |
| 2019/0188067 A1* | 6/2019 | Chen | G06F 11/0751 |
| 2019/0371299 A1 | 12/2019 | Jiang et al. | |
| 2020/0012673 A1* | 1/2020 | Rudzicz | G06K 9/6264 |
| 2020/0044993 A1 | 2/2020 | Wu | |
| 2020/0105381 A1* | 4/2020 | Zhang | G06N 20/20 |
| 2020/0219617 A1* | 7/2020 | Eleftheriou | G16H 50/20 |
| 2020/0279647 A1* | 9/2020 | Buchard | G06N 7/005 |

FOREIGN PATENT DOCUMENTS

| | | | | |
|---|---|---|---|---|
| CN | 107832047 A | | 3/2018 | |
| CN | 108228637 A | | 6/2018 | |
| CN | 108242266 A | * | 7/2018 | |
| CN | 108491433 A | | 9/2018 | |
| CN | 108509463 A | | 9/2018 | |
| CN | 108595619 A | | 9/2018 | |
| CN | 109002540 A | | 12/2018 | |
| CN | 109036588 A | | 12/2018 | |
| CN | 109147931 A | * | 1/2019 | G06N 20/00 |
| CN | 109271505 A | | 1/2019 | |
| CN | 109313650 A | | 2/2019 | |
| EP | 3270331 A1 | * | 1/2018 | G06F 19/34 |
| WO | WO-2004104919 A2 | * | 12/2004 | G06N 5/046 |
| WO | WO-2015058558 A1 | * | 4/2015 | G06F 16/9535 |
| WO | WO-2019070763 A1 | * | 4/2019 | |
| WO | WO-2019198386 A1 | * | 10/2019 | G06F 40/268 |

OTHER PUBLICATIONS

Mujeeb et al., "Aquabot: A Diagnostic Chatbot for Achluophobia and Autism," (IJACSA) International Journal of Advanced Computer Science and Applications, vol. 8, No. 9, 2017. (Year: 2017).*

* cited by examiner

QUESTION GENERATING METHOD AND APPARATUS, INQUIRING DIAGNOSIS SYSTEM, AND COMPUTER READABLE STORAGE MEDIUM

CROSS-REFERENCE TO RELATED APPLICATIONS

The present application is a U.S. National Stage Application under 35 U.S.C. § 371 of International Patent Application No. PCT/CN2019/078734, filed on May 19, 2019, the disclosure of which is hereby incorporated by reference in entirety for all purposes.

TECHNICAL FIELD

The present disclosure relates to the field of computer technology, and in particular, to a question generating method and apparatus, an inquiring diagnosis system, and a computer readable storage medium.

BACKGROUND

With the rapid development of human-computer interaction technology, intelligent inquiring diagnosis has become one of the important research fields of artificial intelligence. An intelligent inquiring diagnosis system collects a patient's symptoms and signs information through human-computer interactions with the patient.

In related technology, many times of interaction with patients are needed to collect comprehensive symptoms and signs information so as to make an accurate diagnosis.

SUMMARY

According to some embodiments of the present disclosure, a question generating apparatus is provided, including at least one processor, the at least one processor being configured to: acquire a candidate question set Q; calculate an information value of each candidate question in the candidate question set Q; and generate at least one question according to the information value of each candidate question.

In some embodiments, generating at least one question includes: selecting a candidate question with the greatest information value from the candidate question set Q as the generated at least one question.

In some embodiments, the at least one processor is configured to acquire the candidate question set Q according to a dialog context; the candidate question set Q includes a first selected number of candidate questions $q_i$, of which correlation degree with the dialog context satisfies a threshold, where i is a positive integer less than or equal to the first selected number; and the generated at least one question includes a dialog question to be asked to a dialog object.

In some embodiments, the information value of each candidate question is positively correlated with an expected value of information amount brought by the candidate question.

In some embodiments, the at least one processor is further configured to acquire an answer $a_j$ corresponding to a candidate question in the candidate question set Q to obtain an answer set A, where j is a positive integer less than or equal to the first selected number, and j=i indicates that the answer $a_j$ corresponds to the candidate question $q_i$.

In some embodiments, the at least one processor is configured to obtain the information value of each candidate question by $$F(q_i \mid \text{context}) = \sum_{a_j \in A} P(a_j \mid \text{context}, q_i) f(\text{context}, q_i, a_j),$$

wherein context represents a dialog context; $f(\text{context}, q_i, a_j)$ represents information amount that each candidate question $q_i$ brings for the dialog context (context); and $P(a_j \mid \text{context}, q_i)$ represents a probability of generating an answer $a_j$ for the dialog context (context) and the candidate question $q_i$.

In some embodiments, information amount $f(\text{context}, q_i, a_j)$ brought by each candidate question $q_i$ is positively correlated with the correlation degree between the candidate question $q_i$ and the corresponding dialog context (context), and is positively correlated with the accuracy of the answer $a_j$ in the answer set A; and the probability $P(a_j \mid \text{context}, q_i)$ is positively correlated with the similarity between the candidate questions $q_i$ and each of the other candidate questions, and is positively correlated with the similarity between a predicted answer to the candidate question $q_i$ and the answer $a_j$ in the answer set A.

In some embodiments, the probability $P(a_j \mid \text{context}, q_i)$ is expressed as $P(a_j \mid \text{context}, q_i) \propto \exp(\cos(G(\text{context}, q_i), a_j)) \times \cos(q_i, q_j)$, wherein $\cos(q_i, q_j)$ represents the similarity between candidate questions $q_i$ and $q_j$; $G(\text{context}, q_i)$ represents the predicted answer of the candidate question $q_i$; and $\cos(G(\text{context}, q_i), a_j)$ represents the similarity between the predicted answer to the candidate question $q_i$ and the answer $a_j$ in the answer set A.

In some embodiments, the predicted answer to the candidate question $q_i$ is obtained by using a first recurrent neural network; and information amount $f(\text{context}, q_i, a_j)$ brought by each candidate question $q_i$ is calculated by using a second recurrent neural network.

In some embodiments, the first recurrent neural network is a gated recurrent unit network; and the second recurrent neural network is a long-short-term memory network.

In some embodiments, the at least one processor is further configured to: based on a corpus and a loss function, perform training by using a stochastic gradient descent method to form the first recurrent neural network and the second recurrent neural network, wherein the corpus includes a dialog context for training Tcontext, a candidate question set for training TQ, and an answer set for training TA; the candidate question set for training TQ includes a second selected number of candidate questions for training $q_l$; and the answer set for training TA includes answers $a_m$ corresponding to the candidate questions in the candidate question set for training TQ, where l is a positive integer less than or equal to the second selected number, and m is a positive integer less than or equal to the second selected number; and the loss function is negatively correlated with the similarity of each candidate question $q_l$ and each of the other candidate questions, is negatively correlated with the similarity between a predicted answer of the candidate question $q_l$ and the answers $a_m$ in the answer set for training TA, is negatively correlated with the correlation degree between the candidate question $q_l$ and the corresponding dialog context for training Tcontext, and is negatively correlated with the accuracy of the answers $a_m$.

In some embodiments, the loss function is expressed as $$Loss=\Sigma_{l,m}(L(Tcontext,q_l,a_m),+L(y_l,Tcontext,q_l,a_m)),$$
wherein $$L(Tcontext,q_l,a_m)=-\cos(G(Tcontext,q_l),a_m)-\Sigma_{q_n \in TQ}\\ \cos(G(Tcontext,q_l),a_n)\times\cos(q_l,q_n), \text{ and}$$

$$L(y_l,Tcontext,q_l,a_m)=-y_l\log(\sigma(LSTM(Tcontext,q_l,a_m))),$$

wherein $\cos(q_l, q_n)$ represents the similarity between candidate questions $q_l$ and $q_n$; $G(Tcontext, q_l)$ represents predicted answers to the candidate questions $q_l$; $\cos(G(Tcontext, q_l), a_m)$ represents the similarity between the predicted answers to the candidate questions $q_l$ and the answers $a_m$; $\cos(G(Tcontext, q_l), a_n)$ represents the similarity between the predicted answers to the candidate questions $q_l$ and answers $a_n$ in the answer set for training, where n is a positive integer less than or equal to the second selected number; $y_l=1$ if l is equal to m, and $y_l=0$ if l is not equal to m; $\sigma$ is a sigmoid function; and $LSTM(Tcontext, q_l, a_m)$ represents information amount brought about by the candidate questions $q_l$ for the context for training Tcontext.

According to some other embodiments of the present disclosure, an inquiring diagnosis system is provided, including the question generating apparatus in any embodiment described above, wherein the dialog is a dialog interaction in medical inquiring diagnosis, and the dialog object is a patient; and the question generating apparatus is configured to generate an inquiring diagnosis question to be asked to the patient, according to the inquiring diagnosis context.

In some embodiments, the inquiring diagnosis system further includes: an input device configured to acquire the inquiring diagnosis context; and an output device configured to output the inquiring diagnosis question.

In some embodiments, the inquiring diagnosis context includes description by the patient.

In some embodiments, the inquiring diagnosis context includes an inquiring diagnosis question that has been asked to the patient.

In some other embodiments of the present disclosure, a question generating method is provided, including: acquiring a candidate question set Q; calculating an information value of each candidate question in the candidate question set Q; and generating at least one question based on the information value of each candidate question.

In some embodiments, generating at least one question includes: selecting a candidate question with the greatest information value from the candidate question set Q as a question to be generated.

In some embodiments, the candidate question set Q is acquired according to a dialog context; the candidate question set Q includes a first selected number of candidate questions $q_i$ whose correlation degree with the dialog context satisfies a threshold, where i is a positive integer less than or equal to the first selected number; and the at least one question to be generated includes a dialog question to be addressed to a dialog object.

In some embodiments, the information value of each candidate question in the candidate question set Q is calculated according to an expected value of information amount brought by each candidate question.

In some embodiments, the question generating method further includes: acquiring answers $a_j$ corresponding to the candidate questions in the candidate question set Q to obtain an answer set A, where j is a positive integer less than or equal to the first selected number, and j=i indicates that the answers $a_j$ are answers corresponding to the candidate questions $q_i$.

In some embodiments, the information value of each candidate question is expressed as $$F(q_i \mid context) = \sum_{a_j \in A} P(a_j \mid context, q_i)f(context, q_i, a_j),$$

wherein information amount brought by each candidate question is $f(context, q_i, a_j)$, which represents information amount that the candidate question $q_i$ brings for a dialog context (context); and $P(a_j|context, q_i)$ represents the probability of generating an answer $a_j$ for the dialog context (context) and the candidate question $q_i$.

In some embodiments, information amount $f(context, q_i, a_j)$ brought by each candidate question is positively correlated with the correlation degree between the candidate question $q_i$ and the corresponding dialog context (context), and is positively correlated with the accuracy of the answer $a_j$ in the answer set A; and the probability $P(a_j|context, q_i)$ is positively correlated with the similarity between the candidate questions $q_i$ and each of the other candidate questions, and is positively correlated with the similarity between a predicted answer to the candidate question $q_i$ and the answer $a_j$ in the answer set A.

In some embodiments, the predicted answer to the candidate question qi is obtained by using a first recurrent neural network; and information amount $f(context, q_i, a_j)$ brought by each candidate question $q_i$ is calculated by using a second recurrent neural network.

In some embodiments, the question generating method further includes: based on a corpus and a loss function, performing training by using a stochastic gradient descent method to form the first recurrent neural network and the second recurrent neural network, wherein the corpus includes a dialog context for training Tcontext, a candidate question set for training TQ, and an answer set for training TA; the candidate question set for training TQ includes a second selected number of candidate questions for training $q_l$; and the answer set for training TA includes answers $a_m$ corresponding to the candidate questions in the candidate question set for training TQ, where l is a positive integer less than or equal to the second selected number, and m is a positive integer less than or equal to the second selected number; and the loss function is negatively correlated with the similarity of each candidate question $q_l$ and each of the other candidate questions, is negatively correlated with the similarity between a predicted answer of the candidate question $q_l$ and the answers $a_m$ in the answer set for training TA, is negatively correlated with the correlation degree between the candidate question $q_l$ and the corresponding dialog context for training Tcontext, and is negatively correlated with the accuracy of the answers $a_m$.

According to some other embodiments of the present disclosure, a computer readable storage medium is provided, which stores a computer program, wherein the computer program, when executed by a processor, implements the question generating method in any foregoing embodiment.

Other features and advantages of the present disclosure will become apparent from the following detailed description of exemplary embodiments of the present disclosure with reference to the accompanying drawings.

BRIEF DESCRIPTION OF THE DRAWINGS

The accompanying drawings, which form a part of the specification, illustrates embodiments of the present disclosure, and are used, together with the description, to explain principles of the present disclosure.

The present disclosure can be understood more clearly with reference to the drawings, based on the following detailed description, wherein.

It should be understood that the dimensions of the various parts shown in the figures are not drawn to actual scale. In addition, same or similar reference numerals represent same or similar components.

DETAILED DESCRIPTION

Figure 1:
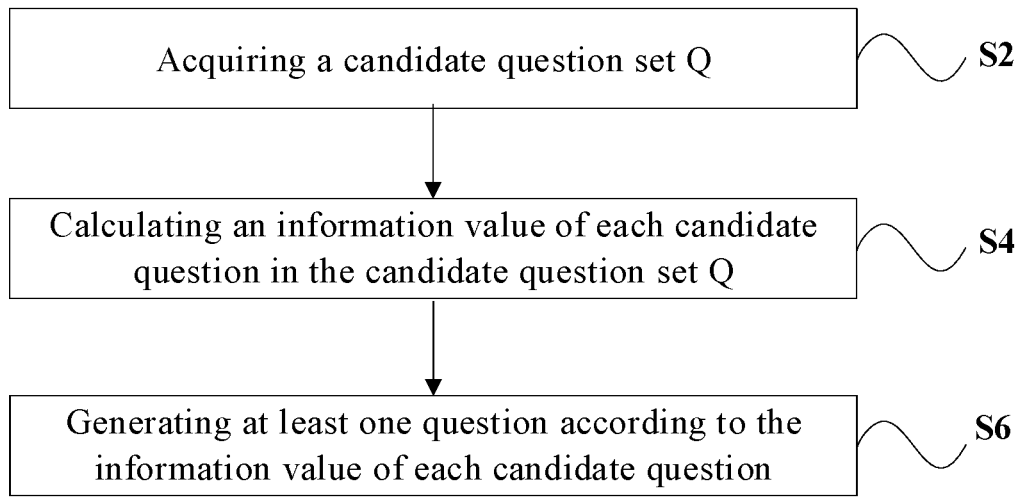
FIG. 1 is a flow diagram illustrating a question generating method according to an embodiment of the present disclosure.

Various exemplary embodiments of the present disclosure will be described in detail with reference to the accompanying drawings in the following. The following description of the exemplary embodiments is merely illustrative in nature and is in no way intended to limit this disclosure, its application, or uses. The present disclosure may be implemented in many different forms and is not limited to the embodiments described herein. These embodiments are provided merely for making the present disclosure thorough and complete, and sufficiently expressing the scope of the present disclosure to one of ordinary skill in the art. It should be noted that the relative arrangement of the components and steps set forth in these embodiments are interpreted to be merely illustrative instead of restrictive, unless it is specifically stated otherwise.

All terms (including technical or scientific terms) used in this disclosure have the same meanings as understood by one of ordinary skill in the art, unless otherwise specifically defined. It should also be understood that the terms defined in common dictionaries should be interpreted as having meanings consistent with their meanings in the context of the relevant technologies, but should not be interpreted with idealized or extremely formalized meanings, unless otherwise expressly defined herein.

Techniques, methods and apparatus as known by one of ordinary skill in the relevant art may not be discussed in detail, but are intended to be regarded as a part of the specification where appropriate.

Question-answer based dialogs are very common in various fields. For example, in industries such as hotel and lodging, a resident may ask a receptionist at a front desk of a hotel multiple or multiple rounds of questions; in a word answer or poem relay contest of TV variety shows, a guest may ask questions in succession to a player; and in industries such as telecommunications and cable TVs, a service providers may also provide services, such as customer services through the telephone, to service subscribers.

It may take a lot of dialogs and a long time to locate an accurate answer to a question raised by a user, which will lead to the cost of manpower and time.

For example, in the medical field, the above-mentioned problems are significant. It takes many times of interactions with a patient and a long time to make an accurate diagnosis on a disease, pathogenetic condition, medication, etc. This may cause delayed diagnosis of the patient and a waste of medical resources.

The present disclosure proposes a question generating method capable of obtaining as much information as possible with as few questions as possible, so that accurate diagnosis can be made in a shorter time.

In the following embodiment, an implementation process of the question generating method of the present disclosure is described by using an inquiring diagnosis dialog in the medical field as an example. Those skilled in the art can appreciate that this may also be applied to other question-answer dialog processes.

FIG. 1 is a flow diagram illustrating a question generating method according to an embodiment of the present disclosure. As shown in FIG. 1, the question generating method includes steps S2-S6.

In step S2, a candidate question set Q is acquired.

In some embodiments, the candidate question set Q is acquired according to an inquiring diagnosis context. The inquiring diagnosis context may include description from the patient. The candidate question set Q includes a first selected number of candidate questions $q_i$, of which correlation degree with the inquiring diagnosis context satisfies a threshold, where i is a positive integer less than or equal to the first selected number.

For example, the inquiring diagnosis context may be used as a query, and a first selected number of the query contexts (for example, the first 10 query contexts are selected) that are closest to the inquiring diagnosis context may be retrieved from a corpus by using a text retrieval tool such as whoosh or lucene, to obtain questions $q_i$ corresponding to the retrieved inquiring diagnosis contexts, thus forming the candidate question set Q.

In some embodiments, in step S2, answers $a_j$ corresponding to the candidate questions in the candidate question set Q are also acquired to obtain an answer set A, where j is a positive integer less than or equal to the first selected number. j=i indicates that the answers $a_j$ are answers corresponding to the candidate questions $q_i$.

In step S4, an information value of each candidate question in the candidate question set Q is calculated.

In some embodiments, the information value of each candidate question $q_i$ in the candidate question set Q is calculated according to an expected value of information amount brought by each candidate question $q_i$.

For example, the information value of each candidate question $q_i$ may be expressed as $$F(q_i \mid \text{context}) = \sum_{a_j \in A} P(a_j \mid \text{context}, q_i) f(\text{context}, q_i, a_j),$$

where information amount brought by each candidate question is $f(\text{context}, q_i, a_j)$, which represents information amount that the candidate question $q_i$ brings for the inquiring diagnosis context (context); and $P(a_j \mid \text{context}, q_i)$ represents the probability of generating an answer $a_j$ for the inquiring diagnosis context (context) and the candidate question $q_i$.

In some embodiments, information amount $f(context, q_i, a_j)$ brought by each candidate question $q_i$ is positively correlated with the correlation degree between the candidate question $q_i$ and the corresponding inquiring diagnosis context (context), and is positively correlated with the accuracy of the answer $a_j$ in the answer set A.

$f(context, q_i, a_j)$ reflects information amount when the candidate question $q_i$ and the answer $a_j$ are considered comprehensively. In the case where the candidate question $q_i$ is highly correlated with the inquiring diagnosis context (context) and the answer $a_j$ accurately answers the candidate question $q_i$, $f(context, q_i, a_j)$ is large.

For example, for an inquiring diagnosis context "an ache in the calf", both candidate questions "Are there spasms in the lower limbs?" and "Are there cramps in the calves?" are highly correlated with the inquiring diagnosis context. However, as standard medical terms are used in the candidate question "Are there spasms in the lower limbs?", the question may be not understood due to a lack of medical knowledge, resulting in an answer such as "What does spasm mean?", that is, the accuracy of the answer obtained may be relatively low.

In contrast, for the candidate question "Are there cramps in the calves?", as everyday words that are relatively easy to understand are used therein, an accurate answer such as "My calf cramps once" may be obtained; that is, the accuracy of the answer obtained is relatively high.

Therefore, for the inquiring diagnosis context "an ache in the calf", information amount brought by the candidate question "Are there cramps in the calves?" is larger than that brought by the candidate question "Are there spasms in the lower limbs?".

In some other embodiments, the probability $P(a_j|context, q_i)$ is positively correlated with the similarity between the candidate questions $q_i$ and each of the other candidate questions, and is positively correlated with the similarity between a predicted answer to the candidate question $q_i$ and the answer $a_j$ in the answer set A.

For example, the probability $P(a_j|context, q_i)$ may be expressed as $P(a_j|context, q_i) \propto \exp(\cos(G(context, q_i), a_j)) \times \cos(q_i, q_j)$, where: $\cos(q_i, q_j)$ represents the similarity between candidate questions $q_i$ and $q_j$; $(context, q_i)$ represents the predicted answer of the candidate question $q_i$; $\cos(G(context, q_i), a_j)$ represents the similarity between the predicted answer to the candidate question $q_i$ and the answer $a_j$ in the answer set A; cos represents a cosine similarity, and exp represents an exponential function with a natural constant e as a base.

The inquiring diagnosis context (context), the candidate questions $q_i$ and the answers $a_j$ may be represented by word vectors. Word vector representations of the inquiring diagnosis context (context), the candidate question $q_i$ and the answer $a_j$ may be implemented by using a technique such as word2vector.

In some embodiments, the predicted answer to the candidate question $q_i$ is obtained by using a first recurrent neural network; and information amount $f(context, q_i, a_j))$ brought by each candidate question $q_i$ is calculated by using a second recurrent neural network.

Both the first recurrent neural network and the second recurrent neural network may be gated recurrent unit (GRU) networks or long short-term memory (LSTM) networks. In some embodiments, the first recurrent neural network is a GRU network, and the second recurrent neural network is an LSTM network.

In step S6, at least one question is generated according to the information value of each candidate question.

The generated at least one question may include an inquiring diagnosis question to be asked to the patient.

In some embodiments, a candidate question with the greatest information value is selected from the candidate question set Q as a question to be generated.

For example, each time an inquiring diagnosis question is asked to the patient, a candidate question with the greatest information value is selected. For the next inquiring diagnosis question, the candidate question currently with the greatest information value (that is, the inquiring diagnosis question already asked to the patient) may be added to the inquiring diagnosis context (context), and then the foregoing process of the question generating method is repeated. In this way, a series of questions may be generated with less computation.

In some other embodiments, candidate questions may also be selected by comprehensively considering the sum of the information amounts of multiple questions to be generated. For example, if three inquiring diagnosis questions are to be generated, three inquiring diagnosis questions with the largest sum of information amounts brought thereby may be selected as questions to be generated, according to the information values of the candidate questions. In this way, the overall efficiency of information collection may be improved.

Figure 2:
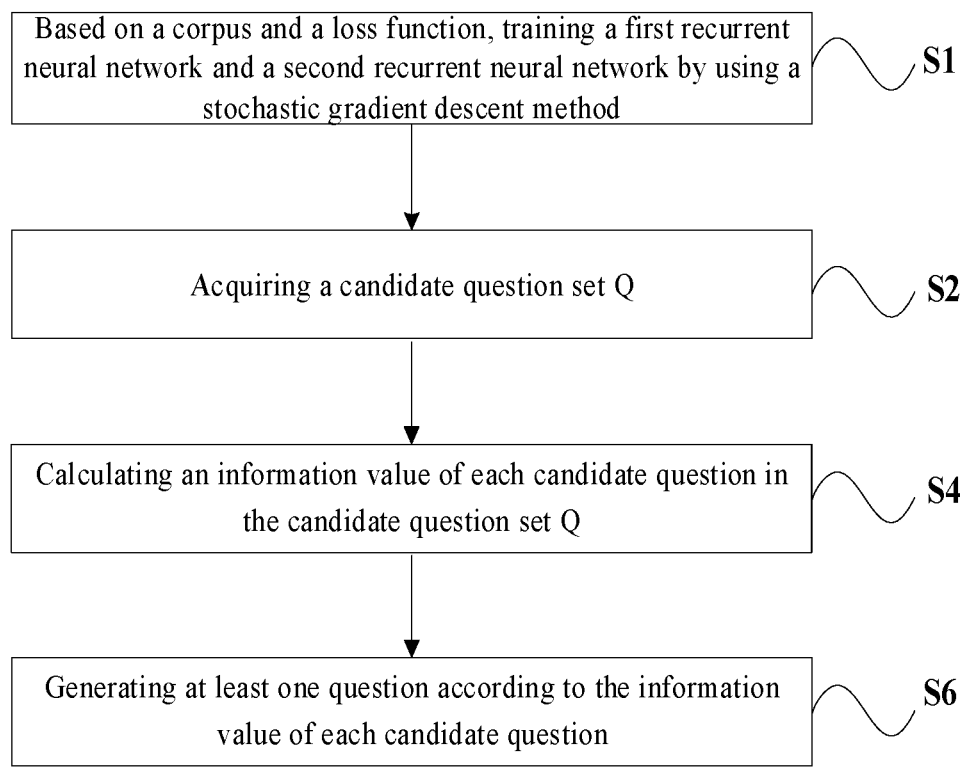
FIG. 2 is a flow diagram illustrating a question generating method according to another embodiments of the present disclosure.

FIG. 2 is a flow diagram illustrating a question generating method according to another embodiments of the present disclosure. FIG. 2 differs from FIG. 1 in that the question generating method in FIG. 2 further includes step S1. Only differences between FIGS. 2 and 1 will be described below, and similarities will not be repeated.

In step S1, based on a corpus and a loss function, training is performed by using a stochastic gradient descent method to form the first recurrent neural network and the second recurrent neural network.

Training samples such as an inquiring diagnosis context for training Tcontext, a candidate question set for training TQ, and an answer set for training TA may be obtained from the corpus in a similar manner of acquiring the candidate question set Q in step S2, to construct a training data set.

The candidate question set for training TQ includes a second selected number of candidate questions for training $q_l$, where l is a positive integer less than or equal to the second selected number. The answer set for training TA includes answers $a_m$ corresponding to the candidate questions in the candidate question set for training TQ, wherein m is a positive integer less than or equal to a second selected number. The second selected number may be set according to training needs.

The corpus may be constructed based on relevant information obtained by a crawler from the Internet, the relevant information including initial description from the patient, questions from a medical person, and the patient's answers to the questions. The information may be stored in the corpus as (C, q, a), where the initial description from the patient corresponds to the inquiring diagnosis context, and may be denoted by C; and for the inquiring diagnosis context, the questions from the medical person are denoted by q; and the patient's answers to the questions q are denoted by a.

For example, a patient on a medical website said "My throat is very painful. I thought it was caused by a cold when I had a cold, but now it's not getting better while my cold is gone . . . ", which may be denoted by C; a doctor asked "How old are you this year? Have you had a similar medical history before? What medicine have you taken . . . ", which may be denoted by $q_1$; the patient responded "23 this year.

I have no similar medical history. I took cold medicine, but I can't remember exactly the names, like roxithromycin, Qingrejiedu granules", which may be denoted by $a_1$; the doctor then asked, "How long has your throat hurt this time?", which may be denoted be $q_2$; and the patient responded to the doctor's follow-up question, "Eight or nine days," which may be denoted by $a_2$. That is, the aforementioned information may be stored as (C, $q_1$, $a_1$, $q_2$, $a_2$).

Although a method of constructing a corpus by using information from the Internet is illustrated above, the required corpus may also be constructed from other sources, for example, based on medical records from medical sites such as hospitals, clinics, etc.

In some embodiments, the loss function is constructed to be negatively correlated with the similarity of each candidate question $q_l$ and each of the other candidate questions, is negatively correlated with the similarity between a predicted answer of the candidate question $q_l$ and the answers $a_m$ in the answer set for training TA, is negatively correlated with the correlation degree between the candidate question $q_l$ and the corresponding inquiring diagnosis context for training Tcontext, and is negatively correlated with the accuracy of the answers $a_m$.

For example, the loss function is expressed as $$\text{Loss} = \Sigma_{l,m}(L(T\text{context},q_l,a_m),+L(y_l,T\text{context},q_l,a_m)),$$
wherein $$L(T\text{context},q_l,a_m) = -\cos(G(T\text{context},q_l),a_m) - \Sigma_{q_n \in TQ} \cos(G(T\text{context},q_l),a_n) \times \cos(q_l,q_n), \text{ and}$$

$$L(y_l,T\text{context},q_l,a_m) = -y_l \log(\sigma(\text{LSTM}(T\text{context},q_l,a_m))).$$

$\cos(q_l, q_n)$ represents the similarity between candidate questions $q_l$ and $q_n$; G (Tcontext, $q_l$) represents predicted answers to the candidate questions $q_l$; $\cos(G(T\text{context}, q_l), a_m)$ represents the similarity between the predicted answers to the candidate questions $q_l$ and the answers $a_m$; $\cos(G(T\text{context}, q_l), a_n)$ represents the similarity between the predicted answers to the candidate questions $q_l$ and answers $a_n$ in the answer set for training, where n is a positive integer less than or equal to the second selected number; $y_l=1$ if l is equal to m, and yl=0 if l is not equal to m; σ is a sigmoid function; and LSTM (Tcontext, $q_l$, $a_m$) represents information amount brought about by the candidate questions $q_l$ for the context for training Tcontext.

In the stochastic gradient descent method, a training data is randomly selected for calculation in the direction of the fastest decline, instead of scanning the entire training data set. In this way, the iteration speed may be increased.

As described above, the GRU network is used in calculation of the probability P ($a_j$|context, $q_i$), so that the training efficiency may be improved; and the LSTM network is used in calculation of information amount f(context, $q_i$, $a_j$), so that better expression performance may be achieved when the amount of data is large.

Figure 3:
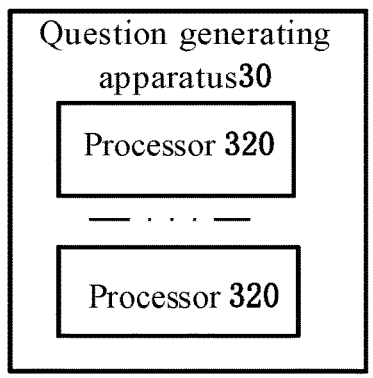
FIG. 3 is a block diagram illustrating a question generating apparatus according to an embodiment of the present disclosure.

FIG. 3 is a block diagram illustrating a question generating apparatus according to an embodiment of the present disclosure. As shown in FIG. 3, the question generating apparatus 30 includes at least one processor 320.

The processor 320 is configured to: acquire a candidate question set Q; calculate an information value of each candidate question in the candidate question set Q; and generate at least one question according to the information value of each candidate question. The processor 320 may execute, for example, the question generating method shown in FIG. 1 or 2.

It is readily understandable to those skilled in the art that the aforementioned question generating apparatus 30 may further include a memory for storing at least a candidate question set.

Figure 4:
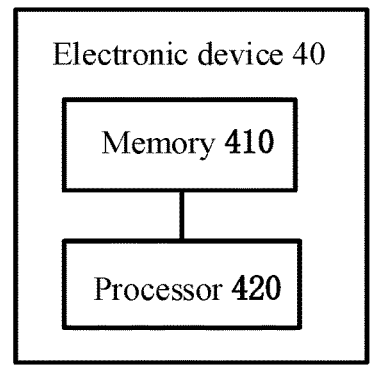
FIG. 4 is a block diagram illustrating an electronic device according to an embodiment of the present disclosure.

FIG. 4 is a block diagram illustrating an electronic device according to an embodiment of the present disclosure.

As shown in FIG. 4, the electronic device 40 includes a memory 410 and a processor 420 coupled to the memory 410. The memory 410 is configured to store instructions for executing an embodiment corresponding to the question generating method. The processor 420 is configured to execute one or more steps in the question generating method in any of the embodiments of the present disclosure based on the instructions stored in the memory 410.

It should be appreciated that the steps in the foregoing question generating method may be implemented by the processor, and may be implemented in any of software, hardware, firmware, or a combination thereof.

In addition to the question generating method and apparatus, embodiments of the present disclosure may also take the form of a computer program product implemented on one or more non-volatile storage media containing computer program instructions. Therefore, an embodiment of the present disclosure further provides a computer readable storage medium storing computer instructions, wherein the instructions, when executed by a processor, implements the question generating method in any of the foregoing embodiments.

An embodiment of the present disclosure further provides an inquiring diagnosis system, which includes the question generating apparatus or electronic device in any one of the foregoing embodiments.

Figure 5:
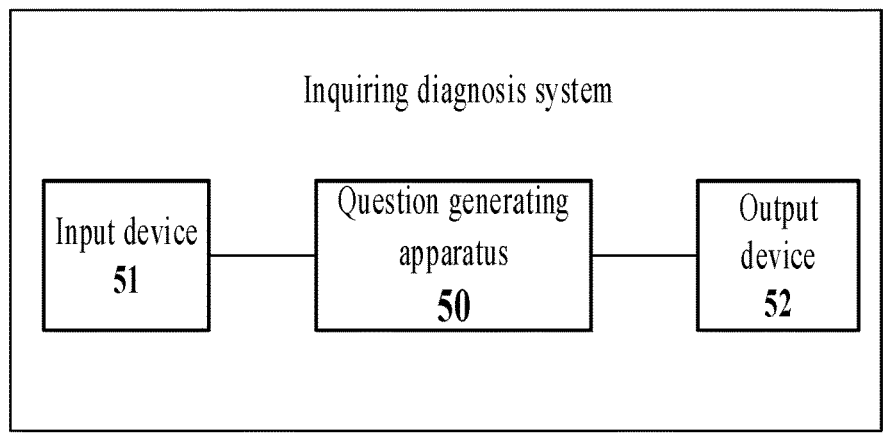
FIG. 5 is a block diagram illustrating an inquiring diagnosis system according to an embodiment of the present disclosure.

FIG. 5 is a block diagram illustrating an inquiring diagnosis system according to an embodiment of the present disclosure.

As shown in FIG. 5, the inquiring diagnosis system 5 includes a question generating apparatus 50. The question generating apparatus 50 is configured to execute the question generating method in any one of the foregoing embodiments. The question generating apparatus 50 may be structurally similar to the aforementioned question generating apparatus 30, and is configured to generate an inquiring diagnosis question to be asked to the patient, according to the inquiring diagnosis context.

In some embodiments, the inquiring diagnosis system 5 further includes: an input device 51 and an output device 52. The input device 51 is configured to acquire the inquiring diagnosis context. For example, the inquiring diagnosis context may be acquired according to multimedia data such as text, sound, or images. The output device 52 is configured to output the inquiring diagnosis question. For example, at least one of a display or a player may be used to output the inquiring diagnosis question.

The input device 51 and the output device 52 may be connected to the question generating apparatus 50 through a network, such as a wireless network, a wired network, and/or any combination of a wireless network and a wired network. The network may include a local area network, the Internet, a telecommunication network, the Internet of Things based on the Internet and/or a telecommunication network, and/or any combination of the aforementioned networks. The wired network may achieve communication through, for example, twisted pair, coaxial cable, or fiber optic transmission, and the wireless network may achieve communication through, for example, a 3G/4G/5G mobile communication network, Bluetooth, Zigbee, or Wi-Fi.

The inquiring diagnosis system 5 may be implemented in the form of a local service; that is, the input device, the question generating apparatus and the output device are located on the user side. The inquiring diagnosis system 5 may also be implemented in the form of a cloud service, that is, the input device and the output device are located on the user side, the question generating apparatus is located in the cloud, and the question generating apparatus in the cloud may provide services to multiple users at the same time or in a time-sharing manner.

Figure 6:
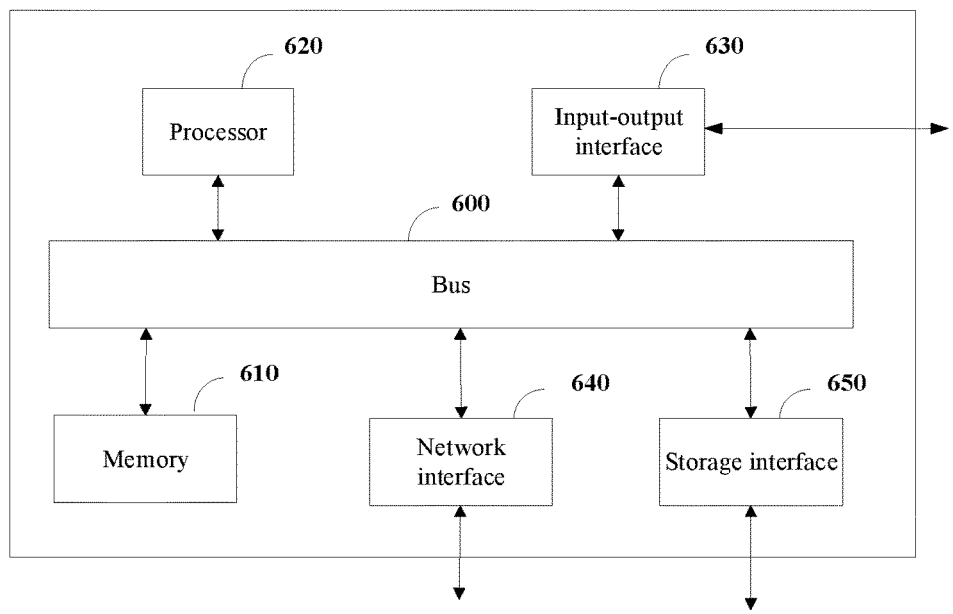
FIG. 6 is a block diagram illustrating a computer system implementing some embodiments of the present disclosure.

FIG. 6 is a block diagram illustrating a computer system implementing some embodiments of the present disclosure.

As shown in FIG. 6, the computer system may be implemented in the form of a general-purpose computing device, and the computer system may be used to implement the question generating apparatus of the foregoing embodiment. The computer system includes a memory 610, a processor 620, and a bus 600 connecting different system components.

The memory 610 may include, for example, a system memory, a non-volatile storage medium, or the like. The system memory stores, for example, an operating system, an application program, a boot loader, and other programs. The system memory may include a volatile storage medium, such as a random access memory (RAM) and/or cache memory. The non-volatile storage medium stores, for example, instructions for executing a corresponding embodiment of a display method. The non-volatile storage media includes, but is not limited to, a magnetic disk memory, an optical memory, a flash memory or the like.

The processor 620 may be implemented in the form of a general-purpose processor, a digital signal processor (DSP), an application specific integrated circuit (ASIC), a field programmable gate array (FPGA) or other programmable logic device, or discrete hardware components such as discrete gates or transistors. Correspondingly, each module such as a judgment module and a determination module may be implemented by a central processing unit (CPU) running instructions for executing corresponding steps in the memory, or by a dedicated circuit that executes corresponding steps.

The bus 600 may use any of various bus structures. For example, the bus structure includes, but is not limited to, an industry standard architecture (ISA) bus, a micro-channel architecture (MCA) bus, or a peripheral component interconnect (PCI) bus.

The computer system may further include an input-output interface 630, a network interface 640, a storage interface 650, and the like. These interfaces 630, 640, 650 and the memory 610 and the processor 620 may be connected through the bus 600. The input/output interface 630 may provide a connection interface for input/output devices such as a display, a mouse, and a keyboard. The network interface 640 provides a connection interface for various networked devices. The storage interface 640 provides a connection interface for external storage devices such as a floppy disk, a U disk, and an SD card.

So far, various embodiments of the present disclosure have been described in detail. To avoid obscuring the concept of the present disclosure, some details known in the art are not described. It will be fully apparent to those skilled in the art from the foregoing description how to carry out the technical solutions disclosed herein.

Although some specific embodiments of the present disclosure have been described in detail by way of example, it should be understood by those skilled in the art that the foregoing examples are for purposes of illustration only and are not intended to limit the scope of the present disclosure.

It will be understood by those skilled in the art that modifications may be made to the above embodiments or equivalents may be substituted for some technical features thereof without departing from the scope and spirit of the present disclosure. The scope of the present disclosure is defined by the appended claims.

What is claimed is:

1. A question generating apparatus, comprising at least one processor, the at least one processor being configured to:
   acquire a candidate question set Q according to a dialog context, wherein the candidate question set Q comprises a first selected number of candidate questions $q_i$, of which correlation degree with the dialog context satisfies a threshold, where i is a positive integer less than or equal to the first selected number;
   acquire an answer $a_j$ corresponding to a candidate question in the candidate question set Q to obtain an answer set A, where j is a positive integer less than or equal to the first selected number, and j=i indicates that the answer a corresponds to the candidate question $q_i$;
   calculate an information value of each candidate question in the candidate question set Q, comprising:
      obtaining a predicted answer to the candidate question $q_i$ by using a first recurrent neural network;
      calculating a probability of generating an answer $a_j$ for the dialog context and the candidate question $q_i$ according to a similarity between the candidate questions $q_i$ and each of the other candidate questions;
      calculating an information amount brought by each candidate question $q_i$ by using a second recurrent neural network according to the probability of generating the answer $a_j$ for the dialog context and the information amount brought by each candidate question $q_i$; and
   generate at least one question according to the information value of each candidate question,
   wherein the at least one processor is further configured to:
      based on a corpus and a loss function, perform training by using a stochastic gradient descent method to form the first recurrent neural network and the second recurrent neural network, and wherein the corpus comprises a dialog context for training Tcontext, a candidate question set for training TQ, and an answer set for training TA.

2. The question generating apparatus according to claim 1, wherein generating at least one question comprises:
   selecting a candidate question with the greatest information value from the candidate question set Q as the generated at least one question.

3. The question generating apparatus according to claim 1, wherein
   the generated at least one question comprises a dialog question to be asked to a dialog object.

4. The question generating apparatus according to claim 1, wherein the information value of each candidate question is positively correlated with an expected value of information amount brought by the candidate question.

5. The question generating apparatus according to claim 1, wherein:
   the first recurrent neural network is a gated recurrent unit network; and
   the second recurrent neural network is a long-short-term memory network.

6. The question generating apparatus according to claim 1, wherein the at least one processor is configured to obtain the information value of each candidate question by $$F(q_i \mid \text{context}) = \sum_{a_j \in A} P(a_j \mid \text{context}, q_i) f(\text{context}, q_i, a_j),$$

where:
context represents a dialog context;
f(context, $q_i$, $a_j$) represents information amount that each candidate question $q_i$ brings for the dialog context (context); and
P($a_j$|context, $q_i$) represents a probability of generating an answer $a_j$ for the dialog context (context) and the candidate question $q_i$.

7. The question generating apparatus according to claim 6, wherein:
the information amount f(context, $q_i$, $a_j$) brought by each candidate question $q_i$ is positively correlated with a correlation degree between the candidate question $q_i$ and the corresponding dialog context (context), and is positively correlated with accuracy of the answer $a_j$ in the answer set A; and
the probability P($a_j$|context, $q_i$) is positively correlated with a similarity between the candidate questions qi and each of the other candidate questions, and is positively correlated with a similarity between a predicted answer to the candidate question $q_i$ and the answer $a_j$ in the answer set A.

8. The question generating apparatus according to claim 7, wherein the probability P($a_3$|context, $q_i$) is expressed as $$P(a_j|\text{context},q_i) \propto \exp(\cos(G(\text{context},q_i),a_j)) \times \cos(q_i, q_j), \text{ where:}$$

$\cos(q_i, q_j)$ represents the similarity between candidate questions $q_i$ and $q_j$;
G(context, $q_i$) represents the predicted answer of the candidate question $q_i$; and
$\cos(G(\text{context}, q_i), a_j)$ represents the similarity between the predicted answer to the candidate question $q_i$ and the answer $a_j$ in the answer set A.

9. The question generating apparatus according to claim 1, wherein:
the candidate question set for training TQ comprises a second selected number of candidate questions for training $q_l$;
the answer set for training TA comprises an answer $a_m$ corresponding to the candidate question in the candidate question set for training TQ, where l is a positive integer less than or equal to the second selected number, and m is a positive integer less than or equal to the second selected number; and
the loss function is negatively correlated with a similarity of each candidate question $q_l$ and each of the other candidate questions, is negatively correlated with a similarity between a predicted answer of the candidate question $q_l$ and the answer $a_m$ in the answer set for training TA, is negatively correlated with a correlation degree between the candidate question $q_l$ and the corresponding dialog context for training Tcontext, and is negatively correlated with accuracy of the answer $a_m$.

10. The question generating apparatus according to claim 9, wherein the loss function is expressed as $$s = \Sigma_{l,m}(L(T\text{context},q_l,a_m) + L(y_l,T\text{context},q_l,a_m)),$$

$$L(T\text{context},q_l,a_m) = -\cos(G(T\text{context},q_l),a_m) - \Sigma_{q_n \in TQ} \cos(G(T\text{context},q_l),a_n) \times \cos(q_l,q_n), \text{ and}$$

$$L(y_l,T\text{context},q_l,a_m) = -y_l \log(\sigma(\text{LSTM}(T\text{context},q_l,a_m))),$$

where:
$\cos(q_l, q_n)$ represents a similarity between candidate questions $q_l$ and $q_n$,
G(Tcontext, $q_l$) represents a predicted answer to the candidate question $q_l$,
$\cos(G(T\text{context}, q_l), a_m)$ represents a similarity between the predicted answer to the candidate question qi and the answer $a_m$,
$\cos(G(T\text{context}, q_l), a_n)$ represents a similarity between the predicted answer to the candidate questions $q_l$ and answer $a_n$ in the answer set for training, where n is a positive integer less than or equal to the second selected number;
$y_l$=1 if l is equal to m, and $y_l$=0 if l is not equal to m;
σ is a sigmoid function; and
LSTM(Tcontext, $q_l$, $a_m$) represents information amount brought by the candidate question $q_l$ for the context for training Tcontext.

11. An inquiring diagnosis system, comprising the question generating apparatus according to claim 1, wherein the dialog is a dialog interaction in medical inquiring diagnosis, the dialog object is a patient, and the question generating apparatus is configured to generate an inquiring diagnosis question to be asked to the patient, according to an inquiring diagnosis context.

12. The inquiring diagnosis system according to claim 11, further comprising:
an input device configured to acquire the inquiring diagnosis context; and
an output device configured to output the inquiring diagnosis question.

13. The question generating apparatus according to claim 11, wherein the inquiring diagnosis context comprises description from the patient.

14. The question generating apparatus according to claim 11, wherein the inquiring diagnosis context comprises an inquiring diagnosis question that has been asked to the patient.

15. A question generating method, comprising:
acquiring a candidate question set Q according to a dialog context, wherein the candidate question set Q comprises a first selected number of candidate questions $q_i$, of which correlation degree with the dialog context satisfies a threshold, where i is a positive integer less than or equal to the first selected number;
acquiring an answer $a_j$ corresponding to a candidate question in the candidate question set Q to obtain an answer set A, where j is a positive integer less than or equal to the first selected number, and j=i indicates that the answer $a_j$ corresponds to the candidate question qi;
calculating an information value of each candidate question in the candidate question set Q, comprising:
obtaining a predicted answer to the candidate question qi by using a first recurrent neural network;
calculating a probability of generating an answer $a_j$ for the dialog context and the candidate question $q_i$ according to a similarity between the candidate questions $q_i$ and each of the other candidate questions;
calculating an information amount brought by each candidate question $q_i$ by using a second recurrent neural network according to the probability of generating the answer $a_j$ for the dialog context and the information amount brought by each candidate question $q_i$; and generating at least one question based on the information value of each candidate question, wherein the at least one processor is further configured to: based on a corpus and a loss function, perform training by using a stochastic gradient descent method to form the first recurrent neural network and the second recurrent neural network, and wherein the corpus comprises a dialog context for training Tcontext, a candidate question set for training TQ, and an answer set for training TA.

16. The question generating method according to claim 15, wherein generating at least one question comprises:
selecting a candidate question with the greatest information value from the candidate question set Q as the generated at least one question.

17. The question generating method according to claim 15, wherein the information value of each candidate question in the candidate question set Q is calculated according to an expected value of information amount brought by each candidate question.

18. A computer readable non-transitory storage medium, storing a computer program, wherein the computer program, when executed by a processor, implements the question generating method according to claim 15.

* * * * *

UNITED STATES PATENT AND TRADEMARK OFFICE
CERTIFICATE OF CORRECTION

PATENT NO. : 11,600,389 B2
APPLICATION NO. : 16/640267
DATED : March 7, 2023
INVENTOR(S) : Zhenzhong Zhang et al.

It is certified that error appears in the above-identified patent and that said Letters Patent is hereby corrected as shown below:

In the Claims

Column 13, Line 23, Claim 7, delete "qi" and insert -- $q_i$ --

Column 13, Line 29, Claim 8, delete "P($a_3$|context," and insert -- P($a_j$|context, --

Column 14, Line 7, Claim 10, delete "qi" and insert -- $q_i$ --

Signed and Sealed this
Twenty-fifth Day of April, 2023

Katherine Kelly Vidal
*Director of the United States Patent and Trademark Office*